(12) United States Patent
Kwon et al.

(10) Patent No.: US 9,007,590 B2
(45) Date of Patent: Apr. 14, 2015

(54) APPARATUS FOR MEASURING TRANSMITTANCE

(71) Applicant: Samsung Corning Precision Materials Co., Ltd., Gyeongsangbuk-do (KR)

(72) Inventors: Yoon Young Kwon, ChungCheongNam-Do (KR); Kyungwook Park, ChungCheongNam-Do (KR); Jinsu Nam, ChungCheongNam-Do (KR); Jaeyoung Choi, ChungCheongNam-Do (KR)

(73) Assignee: Samsung Corning Precision Materials Co., Ltd., Gumi-Si (KR)

( * ) Notice: Subject to any disclaimer, the term of this patent is extended or adjusted under 35 U.S.C. 154(b) by 147 days.

(21) Appl. No.: 13/743,756

(22) Filed: Jan. 17, 2013

(65) Prior Publication Data

US 2013/0188188 A1    Jul. 25, 2013

(30) Foreign Application Priority Data

Jan. 18, 2012    (KR) .................. 10-2012-0005766

(51) Int. Cl.
*G01N 21/00* (2006.01)
*G01N 21/59* (2006.01)
*G01N 21/31* (2006.01)

(52) U.S. Cl.
CPC ............... *G01N 21/59* (2013.01); *G01N 21/31* (2013.01)

(58) Field of Classification Search
CPC .. G01N 1/59; G01N 2201/065; G01N 21/896
See application file for complete search history.

(56) References Cited

U.S. PATENT DOCUMENTS

2011/0255085 A1    10/2011    Watanabe et al.

FOREIGN PATENT DOCUMENTS

| CN | 102187203 A | 9/2011 |
|---|---|---|
| JP | 07-120323 A | 5/1995 |
| JP | 10-332582 A | 12/1998 |
| JP | 2001-356092 A | 12/2001 |
| JP | 2004-108781 A | 4/2004 |
| KR | 1019870002444 | 5/1987 |
| KR | 1020100000349 A | 1/2010 |

*Primary Examiner* — Tri T Ton
(74) *Attorney, Agent, or Firm* — McDermott Will & Emery LLP

(57) ABSTRACT

An apparatus for measuring transmittance which can realize reliability for measurement of the transmittance of a piece of patterned glass by post dispersion of light. The apparatus includes a light source which is disposed in front of an object that is to be measured, and directs light into the object. An integrating sphere is disposed in the rear of the light source and integrating light incident thereinto. The object is mounted on the front portion of the integrating sphere. A light dispersing part is disposed in the rear of the integrating sphere, and disperses light that has been integrated by and then emitted from the integrating sphere. An optical receiver is disposed adjacent to the light dispersing part, and receives light that has been dispersed by the light dispersing part.

10 Claims, 4 Drawing Sheets

US 9,007,590 B2

APPARATUS FOR MEASURING TRANSMITTANCE

CROSS REFERENCE TO RELATED APPLICATION

The present application claims priority from Korean Patent Application Number 10-2012-0005766 filed on Jan. 18, 2012, the entire contents of which application are incorporated herein for all purposes by this reference.

BACKGROUND OF THE INVENTION

1. Field of the Invention

The present invention relates to an apparatus for measuring transmittance, and more particularly, to an apparatus for measuring the transmittance of a piece of patterned glass, in which reliability for measurement of the transmittance of the patterned glass can be achieved by post dispersion of light.

2. Description of Related Art

Recently, as a counter measure to the shortage of energy resources and environmental pollution, the development of photovoltaic modules is underway on a large scale. The efficiency of photovoltaic modules is influenced by the transmittance of a piece of cover glass. Accordingly, an enormous amount of research and development is underway in order to improve the transmittance of the cover glass, for example, by minimizing the internal absorption ratio using a composition of the cover glass or improving the transmittance using a coating. In addition, in order to improve the transmittance of the cover glass, a piece of patterned glass is formed by imparting a two-dimensional (2D) array pattern on a light incident surface of the cover glass. The patterned glass is being widely used not only for photovoltaic modules, but also for flat panel display devices.

Glass substrate manufacturers conduct real-time precise inspection of the transmittance of a piece of patterned glass which is continuously produced by directing light into the glass during the process in which the patterned glass is being manufactured.

A spectrometer is an apparatus of the related art which is used for measuring the transmittance of a piece of patterned glass. As shown in FIG. 1 and FIG. 2, the spectrometer of the related art is configured as an optical system which includes a light source 11, a light dispersing device 12, an integrating sphere 13 and a detector 14. The ISO 9050 international standards regulate that the transmittance of a glass substrate G with respect to solar light be calculated by respectively multiplying spectral transmittances with weighted spectral sensitivities of a measuring system with respect to a standard light source D65 which is used for measurement. Accordingly, the spectrometer of the related art is realized such that it can represent spectral transmittances of visible light in the range from 380 nm to 780 nm by receiving all of the light and then processing the received light. That is, all spectral transmittances for an object of interest are required in order to measure the transmittance of the glass substrate G using the spectrometer of the related art.

As shown in FIG. 3, for a piece of patterned glass, when light is received using the fixed detector, an accurate transmittance cannot be measured since the light greatly diffuses after it has passed through the patterned glass. This is because, in some cases, when incident light that has passed through the patterned glass G greatly diffuses, the detector 14 fixed to the integrating sphere 13 fails to receive the light, as shown in (a) of FIG. 3. Here, (b) of FIG. 3 shows the shape of a laser beam that has diffused after having passed through a piece of non-patterned glass in order to compare it with (a) of FIG. 3, i.e. the result of the patterned glass.

Therefore, when the transmittance of a piece of patterned glass is measured using a spectrometer of the related art, there is the problem of the unreliability of results. As shown in FIG. 4, this is because the intensity of light that is received by the fixed detector 14 may have a measurement error, attributable to different spectral angles of emergence into the air. In particular, for the patterned glass, angles of emergence have a wide distribution attributable to severe scattering of light that has passed through the patterned glass, leading to different integration paths and aspects depending on wavelengths. Therefore, the possibility that the fixed detector 14 may have an error in the measurement of the intensity of light that it has received is further increased. Specifically, in order to increase the transmittance, a piece of cover glass for crystalline photovoltaic cells has a pattern in the upper surface thereof which reduces reflection and increases the intensity of transmission light. When the cover glass for photovoltaic cells which has this pattern, i.e. the patterned glass, is measured using the spectrometer of the related art which receives light after dispersing it, the transmittance cannot be measured accurately, and the high-transmittance effect of the patterned glass cannot be verified.

FIG. 5 is a graph showing the result of transmittance measurement on a piece of high-transmittance patterned glass using an apparatus for measuring transmittance of the related art. Although the transmittance of the patterned glass was measured to be 87.5%, its simulated transmittance was about to be 92.3%. In addition, as shown in FIG. 6, when a piece of patterned glass G was measured using direct transmission, its transmittance with respect to a mixture of wavelengths was measured about 92.46%. Thus, it can be appreciated that a measurement error occurs when the transmittance of the patterned glass G is measured using the spectrometer of the related art.

However, the approach for measuring transmittance using direct transmission shown in FIG. 6 has a drawback in that spectral transmittances are not obtained. Thus, this approach has a limited ability as an apparatus for determining spectral transmittances of the patterned glass.

Accordingly, the apparatus for measuring transmittance of the related art is apparently limited in its ability for reliably measuring the spectral transmittances of the patterned glass.

The information disclosed in the Background of the Invention section is only for the enhancement of understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide an apparatus for measuring transmittance which can realize reliability for measurement of the transmittance of a piece of patterned glass by post dispersion of light, i.e. dispersing light after it has passed through an object that is to be measured.

In an aspect of the present invention, provided is an apparatus for measuring transmittance. The apparatus includes a light source disposed in front of an object that is to be measured, the light source directing light into the object; an integrating sphere disposed in the rear of the light source and integrating light incident thereinto, the object being mounted on the front portion of the integrating sphere; a light dispersing part disposed in the rear of the integrating sphere, the light dispersing part dispersing light that has been integrated by and then emitted from the integrating sphere; and an optical receiver disposed adjacent to the light dispersing part, the optical receiver receiving light that has been dispersed by the light dispersing part.

In an exemplary embodiment, the light source may include a halogen lamp; an optical filter disposed in the rear of the halogen lamp; a reflector plate disposed in front of the halogen lamp; and a focusing lens disposed in the rear of the optical filter.

In an exemplary embodiment, the halogen lamp, the optical filter, the reflector plate and the focusing lens may be disposed inside a black shield.

In an exemplary embodiment, the light source may further include a first optical fiber disposed in the black shield, the first optical fiber emitting light that has passed through the focusing lens.

In an exemplary embodiment, the apparatus may further include a collimation lens disposed between the light source and the object, the collimation lens converting light that has been emitted from the light source into collimated light.

In an exemplary embodiment, the apparatus may further include an aperture disposed between the collimation lens and the object.

In an exemplary embodiment, the object may closely adjoin the front surface of the integrating sphere.

In an exemplary embodiment, light that has been integrated in the integrating sphere may be emitted toward the light dispersing part via a second optical fiber which is disposed on the rear portion of the integrating sphere.

In an exemplary embodiment, the apparatus may further include a signal processor which calculates a transmittance of the object based on a signal transferred from the optical receiver and displays the calculated transmittance of the object.

In an exemplary embodiment, the object may be a piece of patterned glass.

According to embodiments of the invention, it is possible to realize reliability for measurement of the transmittance of the patterned glass by post dispersion of light. Specifically, it is possible to minimize errors in measuring the transmittance of the patterned glass, which would otherwise occur in the method of the related art which disperses light before receiving it. This consequently makes it possible to measure the spectral transmittances of the patterned glass for a photovoltaic cell, which were impossible to measure using the apparatus for measuring transmittance of the related art.

In addition, it is possible to verify the high-transmission effect depending on the shape and size of the pattern.

Furthermore, it is also possible to reliably measure the transmittance of a variety of samples, such as a piece of plastic or a film, which has a pattern or structural features on the surface thereof.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Figure 1:
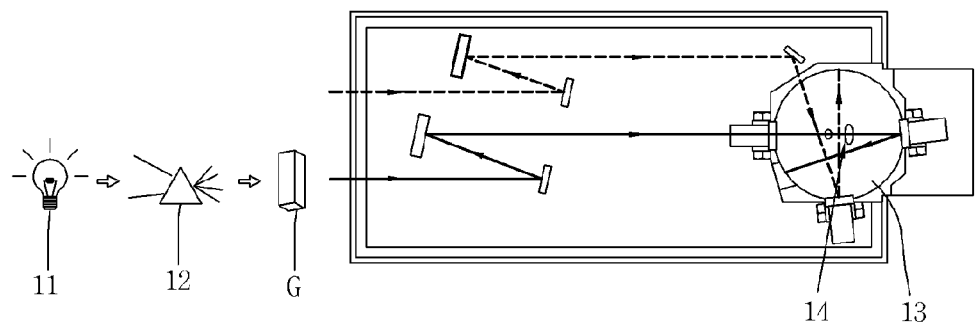
FIG. 1 is a schematic view showing an apparatus for measuring transmittance of the related art.
Figure 2:
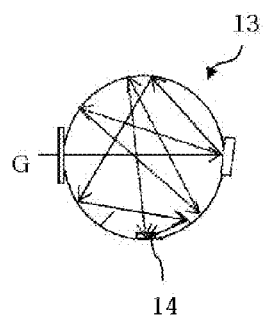
FIG. 2 is a schematic view showing a light path inside an integrating sphere.
Figure 3:
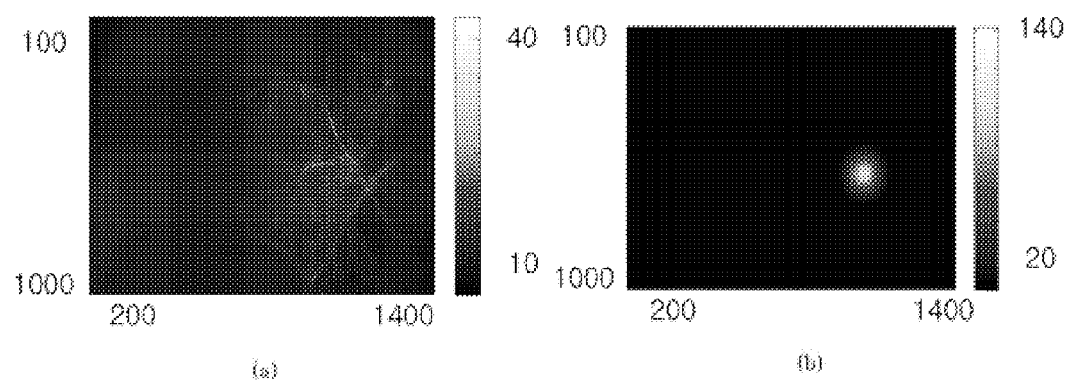
FIG. 3 is pictures showing images of transmission light depending on the sorts of samples.
Figure 4:
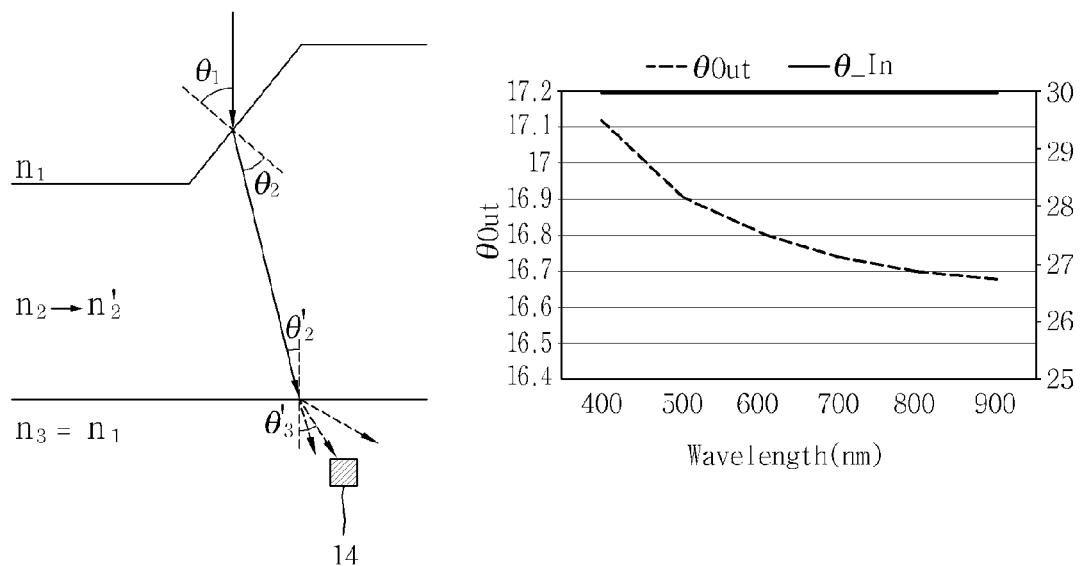
FIG. 4 is a view showing the relationship between an angle of incidence and an angle of emergence at boundary surfaces of a piece of patterned glass.
Figure 5:
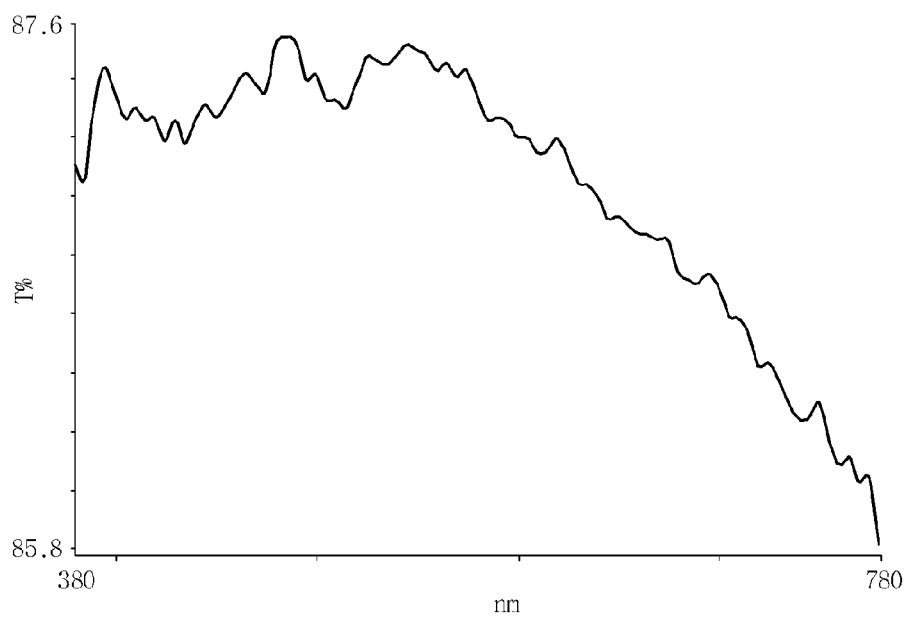
FIG. 5 is a graph showing the result of transmittance measurement on a piece of high-transmittance patterned glass using an apparatus for measuring transmittance of the related art.
Figure 6:
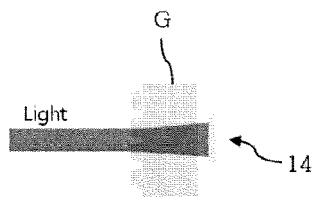
FIG. 6 is a schematic view showing a direct transmission measurement method carried out on a piece of patterned glass.

Reference will now be made in detail to an apparatus for measuring transmittance according to the present invention, embodiments of which are illustrated in the accompanying drawings and described below, so that a person having ordinary skill in the art to which the present invention relates can easily put the present invention into practice.

Throughout this document, reference should be made to the drawings, in which the same reference numerals and signs are used throughout the different drawings to designate the same or similar components. In the following description of the present invention, detailed descriptions of known functions and components incorporated herein will be omitted when they may make the subject matter of the present invention unclear.

Figure 7:
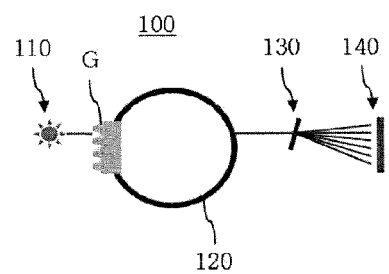
FIG. 7 is a schematic view showing an apparatus for measuring transmittance according to an embodiment of the invention.

As shown in FIG. 7, an apparatus for measuring transmittance according to an embodiment of the invention is an apparatus which measures transmittance based on post dispersion in order to achieve reliability for the measurement of the transmittance of a piece of plastic, a film or a piece of patterned glass which has a concave-convex pattern or structural features. In particular, the patterned glass is used for a cover glass of a photovoltaic cell. The apparatus for measuring transmittance includes a light source 110, an integrating sphere 120, a light dispersing part 130 and an optical receiver 140.

Figure 8:
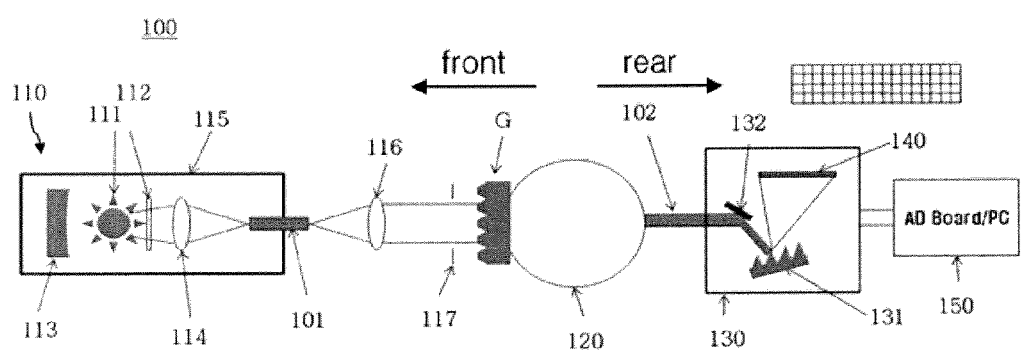
FIG. 8 is a configuration view showing an apparatus for measuring transmittance according to an embodiment of the invention.

The light source 110 is a device which generates light that is required for measurement of the transmittance of an object G that is to be measured, such as a piece of patterned glass. The light source 110 is disposed in front of the object G, and directs the light toward the object G. As shown in FIG. 8, the light source 110 includes a halogen lamp 111, an optical filter 112, a reflector 113 and a focusing lens 114. Here, the optical filter 112 which can reproduce solar light is disposed at the rear of the halogen lamp 111 which has a mixture of wavelengths, and the reflector 113 which reflects the light that has been emitted forward from the halogen lamp 111 toward the object G which is at the rear of the reflector. The focusing lens 114 is disposed at the rear of the optical filter 112, and collects the light that has diverged while passing through the optical filter. Here, the reflector 113 may be made of aluminum (Al).

In addition, it is preferred that components of the light source 110 be disposed inside a black shield 115 in order to prevent the light that has been emitted from the halogen lamp 111 from acting as noise before the light enters the object G. The focusing lens 114 collects the light that has diverged while passing through the optical filter into a first optical fiber 101 which is disposed in the rear section of the black shield 115. Then, the first optical fiber 101 transmits the light that has been emitted from the light source 110 to the object G by minimizing its loss. The first optical fiber 101 is made of glass.

Before the light that has exited the first optical fiber 101 is directed into the object G, it is converted into collimated light while passing through a collimation lens 116 which is disposed between the light source 110 and the object G. The quantity of the collimated light that is to be directed into the object G can be adjusted by an aperture which is disposed between the collimation lens 116 and the object G.

The integrating sphere 120 is a hollow sphere on the inner surface of which a reflecting material is applied, the reflecting material being non-selective with respect to wavelength and being near to perfect diffusion. In addition, the object G that is to be measured is mounted on the front surface of the integrating sphere 120. It is preferred that the object G closely adjoin the front surface of the integrating sphere 120 in order to remove or reduce the loss of scattering light that passes through the aperture 117. Specifically, the light having a mixture of wavelengths that has been emitted from the halogen lamp 111 enters the object G, and the integrating sphere 120 equally integrates the light that has passed through the object G. Here, it is preferred that the size of the integrating sphere 120 and the size of a port through which reference light enters the integrating sphere 120 be optimized by simulation in order to prevent the light from scattering after having passed through the object G. The light having a mixture of wavelengths that has been equally integrated is dispersed depending on the wavelengths, so that the transmittance of the object G is calculated, which will be described in more detail later.

The light that has been integrated in the integrating sphere 120 can be emitted in the direction toward the light dispersing part 130 through a second optical fiber 102 which is disposed on the rear section of the integrating sphere 120 in the state in which light loss is minimized.

The light dispersing part 130 is a device which disperses the light that is emitted through the second optical fiber 102 after having been integrated in the integrating sphere 120. The light dispersing part 130 is disposed at the rear of the integrating sphere 120. With this configuration, this embodiment of the invention realizes the apparatus for measuring transmittance by post dispersion of light, i.e. the apparatus measures the transmittance of the object G after the light passes through the object rather than before the light enters the object G. Unlike the measuring method of the related art, the apparatus for measuring transmittance 100 according to this embodiment of the invention calculates the transmittance of the object G by directing light having a mixture of wavelengths that has been emitted from the halogen lamp 111 to pass through the object G, integrating the dispersed light under the same condition, and then dispersing the integrated light depending on the wavelengths. Due to the configuration in which the object G is mounted on and closely adjoins the front surface of the integrating sphere 120 and the dispersing part 130 is disposed at the rear of the integrating sphere 120, it is possible to minimize errors due to the non-identity of integration aspects depending on the wavelengths inside the integrating sphere 120. This consequently makes it possible to measure the spectral transmittances of the patterned glass for a photovoltaic cell, which were impossible to measure using the apparatus for measuring transmittance of the related art. Furthermore, it becomes possible to verify the high-transmission effect of patterned glass.

The dispersing part 130 may be realized using a grating 131. The grating 131 can disperse all of the integrated light at the same time. A reflector 132 may be disposed at the distal end of the second optical fiber 102, i.e. a portion through which the integrated light exits. The reflector 132 reflects the light that has exited the second optical fiber 102 in the direction toward the grating 131.

The optical receiver 140 is a device which receives the light that has been dispersed by the dispersing part 130. The optical receiver 140 is disposed at one side of the dispersing part 130, i.e. in the direction in which the light is dispersed. The optical receiver 140 can be configured as a charge coupled device (CCD) which can measure the spectral intensities of transmission light that is projected thereon. Here, the optical receiver 140 can measure the intensity of light before the object G is mounted so that this intensity of light is used as a comparison value for the intensity of light after the object G is mounted. In addition, the optical receiver 140 can be configured as one detector which measures the intensity of light. In this case, it is possible to measure the spectral intensities of light by rotating the detector depending on angles at which spectral rays of light are expected to be refracted while the grating 131 is rotating.

The intensities of light measured by the optical receiver must be numerically calculated before being provided to a user. For this, according to an embodiment of the invention, a signal processor 150 may be additionally provided. The signal processor 150 calculates the transmittance of the object G based on an electrical signal transferred from the optical receiver 140, the electrical signal indicating the intensities of light, and displays the calculated transmittance. The signal processor 150 can be configured as a data acquisition (DAQ) system, such as an analog-digital (AD) board or a personal computer (PC).

Figure 9:
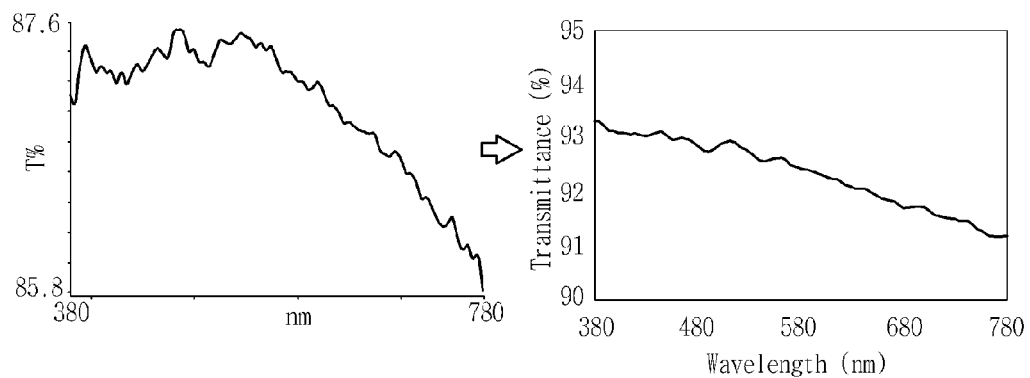
FIG. 9 is graphs comparing transmittance measurements obtained by an apparatus for measuring transmittance according to an embodiment of the invention with transmittance measurements obtained by an apparatus for measuring transmittance of the related art.

FIG. 9 is graphs comparing transmittance measurements of a piece of patterned glass obtained by an apparatus for measuring transmittance according to an embodiment of the invention with transmittance measurements of a piece of patterned glass obtained by an apparatus for measuring transmittance of the related art. The transmittance of the patterned glass measured using the apparatus for measuring transmittance 100 according to an embodiment of the invention was 92%, which is substantially the same as its simulated transmittance of about 92.3%. In contrast, when the transmittance of the patterned glass was measured using the apparatus for measuring transmittance of the related art, it was measured to be 89%, which exhibits a significant margin of error. Thus, it is appreciated that the apparatus for measuring transmittance of the related art cannot reliably measure the transmittance of the patterned glass.

Figure 10:
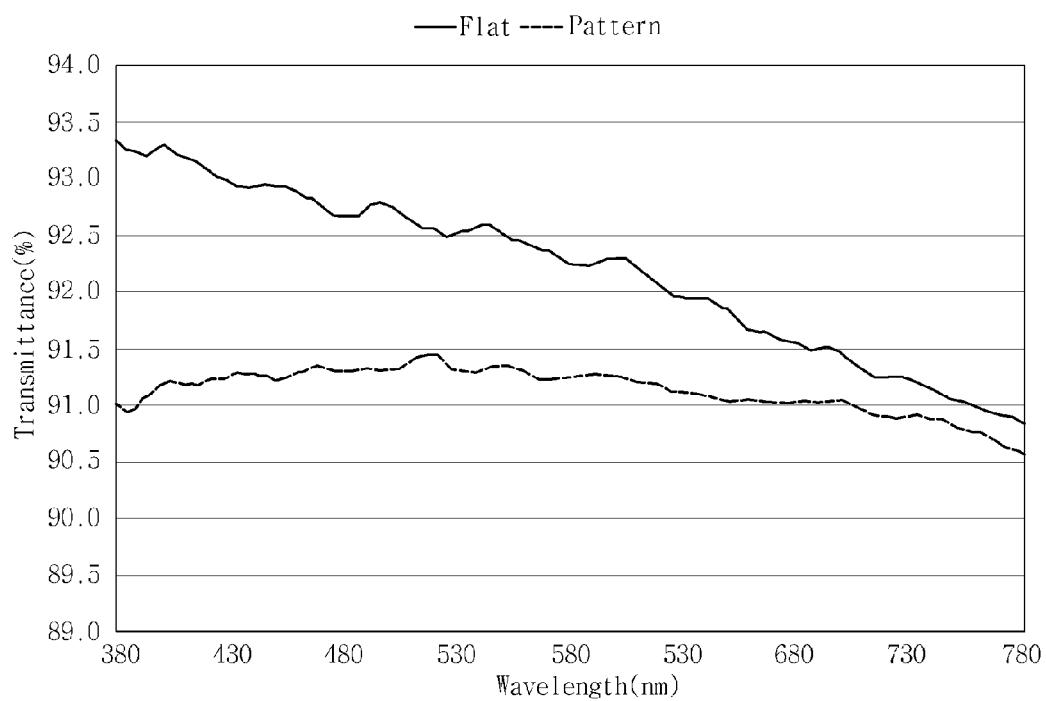
FIG. 10 is a graph comparing transmittance measurements of a piece of flat glass and a piece of patterned glass obtained by an apparatus for measuring transmittance of the related art.

FIG. 10 is a graph comparing transmittance measurements of a piece of flat glass and a piece of patterned glass obtained by an apparatus for measuring transmittance of the related art. The apparatus for measuring transmittance 100 according to an embodiment of the invention can reliably measure not only the transmittance of the patterned glass but also the transmittance of the flat glass. Furthermore, it is also possible to reliably measure the transmittance of a variety of samples, such as a piece of plastic or a film, which has a concave-convex pattern or structural features on the surface thereof.

The foregoing descriptions of specific exemplary embodiments of the present invention have been presented with respect to the certain embodiments and drawings. They are not intended to be exhaustive or to limit the invention to the precise forms disclosed, and obviously many modifications and variations are possible for a person having ordinary skill in the art in light of the above teachings.

It is intended therefore that the scope of the invention not be limited to the foregoing embodiments, but be defined by the Claims appended hereto and their equivalents.

What is claimed is:

1. An apparatus for measuring transmittance, comprising:
   a light source disposed in front of an object that is to be measured, the light source directing light into the object;
   an integrating sphere disposed in one side of the light source and integrating light incident thereinto, the object being mounted on a front portion of the integrating sphere, and between the light source and the integrating sphere;
   a light dispersing part disposed in a rear portion of the integrating sphere, wherein, the rear portion of the integrating sphere being opposite to the front portion of the integrating sphere, and the front portion of the integrating sphere being close to the light source, the light dispersing part dispersing light that has been integrated by and then emitted from the integrating sphere; and
   an optical receiver disposed adjacent to the light dispersing part, the optical receiver receiving light that has been dispersed by the light dispersing part.

2. The apparatus for measuring transmittance of claim 1, wherein the light source comprises:
   a halogen lamp;
   an optical filter disposed in the rear of the halogen lamp;
   a reflector plate disposed in front of the halogen lamp; and
   a focusing lens disposed in the rear of the optical filter.

3. The apparatus for measuring transmittance of claim 2, wherein the halogen lamp, the optical filter, the reflector plate and the focusing lens are disposed inside a black shield.

4. The apparatus for measuring transmittance of claim 3, wherein the light source further comprises a first optical fiber disposed in the black shield, the first optical fiber emitting light that has passed through the focusing lens.

5. The apparatus for measuring transmittance of claim 1, further comprising a collimation lens disposed between the light source and the object, the collimation lens converting light that has been emitted from the light source into collimated light.

6. The apparatus for measuring transmittance of claim 5, further comprising an aperture disposed between the collimation lens and the object.

7. The apparatus for measuring transmittance of claim 1, wherein the object closely adjoins a front surface of the integrating sphere.

8. The apparatus for measuring transmittance of claim 1, wherein light that has been integrated in the integrating sphere is emitted toward the light dispersing part via a second optical fiber which is disposed on a rear portion of the integrating sphere.

9. The apparatus for measuring transmittance of claim 1, further comprising a signal processor which calculates a transmittance of the object based on a signal transferred from the optical receiver and displays the calculated transmittance of the object.

10. The apparatus for measuring transmittance of any one of claims 1 to 9, wherein the object is a piece of patterned glass.

* * * * *